(12) United States Patent
Haskins et al.

(10) Patent No.: US 9,655,655 B2
(45) Date of Patent: May 23, 2017

(54) TWO STEP LOCKING SCREW ASSEMBLY

(75) Inventors: Tyler Haskins, Conshohocken, PA (US); Mohit Prajapati, Blue Bell, PA (US)

(73) Assignee: Aesculap Implant Systems, LLC, Center Valley, PA (US)

( * ) Notice: Subject to any disclaimer, the term of this patent is extended or adjusted under 35 U.S.C. 154(b) by 919 days.

(21) Appl. No.: 13/586,344

(22) Filed: Aug. 15, 2012

(65) Prior Publication Data

US 2013/0066380 A1    Mar. 14, 2013

Related U.S. Application Data

(60) Provisional application No. 61/524,116, filed on Aug. 16, 2011.

(51) Int. Cl.
*A61B 17/70* (2006.01)
*A61B 17/86* (2006.01)

(52) U.S. Cl.
CPC ...... *A61B 17/7035* (2013.01); *A61B 17/7032* (2013.01); *A61B 17/7037* (2013.01); *A61B 17/8685* (2013.01)

(58) Field of Classification Search
USPC .................. 606/264–278, 305–308, 328
See application file for complete search history.

(56) References Cited

U.S. PATENT DOCUMENTS

| | | | |
|---|---|---|---|
| 6,077,262 A * | 6/2000 | Schlapfer et al. | 606/305 |
| 6,755,829 B1 * | 6/2004 | Bono et al. | 606/308 |
| 6,786,903 B2 * | 9/2004 | Lin | 606/23 |
| 6,896,677 B1 * | 5/2005 | Lin | 606/266 |
| 7,081,117 B2 | 7/2006 | Bono | |
| 7,780,703 B2 | 8/2010 | Yuan | |
| 7,780,704 B2 | 8/2010 | Markworth | |
| 7,785,354 B2 | 8/2010 | Biedermann | |
| 7,785,356 B2 | 8/2010 | Biedermann | |
| 7,789,895 B2 | 9/2010 | Heinz | |
| 7,789,896 B2 | 9/2010 | Jackson | |
| 7,789,900 B2 | 9/2010 | Levy | |
| 7,794,476 B2 | 9/2010 | Wisnewski | |
| 7,794,477 B2 | 9/2010 | Melkent | |
| 7,819,901 B2 * | 10/2010 | Yuan et al. | 606/264 |
| 7,967,850 B2 * | 6/2011 | Jackson | 606/301 |

(Continued)

FOREIGN PATENT DOCUMENTS

WO    WO 01/52758    7/2001

OTHER PUBLICATIONS

U.S. Appl. No. 11/961,379, Non Final Office Action mailed Oct. 17, 2012.
"DI Independent Locking Technology", DePuy Spine, Jan. 2006.

*Primary Examiner* — Matthew Lawson
*Assistant Examiner* — Amy Sipp
(74) *Attorney, Agent, or Firm* — RatnerPrestia

(57) ABSTRACT

A two step locking screw assembly includes a receiving member for receiving a fixation member and an anchor having an enlarged portion and a shank. The enlarged portion of the anchor may be seated in the receiving member. An insert may also extend inside the receiving member. An outer fastener may be positioned in the receiving member. The outer fastener may include a central opening and a pair of ramped flanges. An inner fastener may be disposed inside the central opening of the outer fastener.

15 Claims, 5 Drawing Sheets

(56) References Cited

U.S. PATENT DOCUMENTS

| | | | |
|---|---|---|---|
| 8,048,124 B2* | 11/2011 | Chin et al. | 606/264 |
| 8,062,340 B2* | 11/2011 | Berrevoets et al. | 606/270 |
| 8,162,989 B2* | 4/2012 | Khalili | 606/266 |
| 8,221,472 B2* | 7/2012 | Peterson et al. | 606/270 |
| 8,343,191 B2* | 1/2013 | Matthis et al. | 606/264 |
| 8,465,528 B2* | 6/2013 | Schumacher | 606/273 |
| 8,690,925 B2* | 4/2014 | Biedermann et al. | 606/272 |
| 2002/0143341 A1* | 10/2002 | Biedermann et al. | 606/73 |
| 2004/0162560 A1 | 8/2004 | Raynor | |
| 2004/0167525 A1* | 8/2004 | Jackson | 606/73 |
| 2004/0193160 A1 | 9/2004 | Richelsoph | |
| 2006/0149233 A1 | 7/2006 | Richelsoph | |
| 2006/0149241 A1 | 7/2006 | Richelsoph | |
| 2006/0161152 A1* | 7/2006 | Ensign et al. | 606/61 |
| 2007/0260246 A1* | 11/2007 | Biedermann | 606/61 |
| 2008/0021473 A1* | 1/2008 | Butler et al. | 606/63 |
| 2008/0058811 A1 | 3/2008 | Alleyne | |
| 2008/0086131 A1 | 4/2008 | Daly | |
| 2008/0086132 A1 | 4/2008 | Biedermann | |
| 2008/0086138 A1 | 4/2008 | Stone | |
| 2008/0114362 A1 | 5/2008 | Justis | |
| 2008/0114400 A1 | 5/2008 | Dant | |
| 2008/0125788 A1 | 5/2008 | Cohen | |
| 2008/0140121 A1 | 6/2008 | McLeer | |
| 2008/0147121 A1 | 6/2008 | Justis | |
| 2008/0147122 A1 | 6/2008 | Jackson | |
| 2008/0154308 A1 | 6/2008 | Sherman | |
| 2008/0215100 A1 | 9/2008 | Matthis et al. | |
| 2008/0294202 A1* | 11/2008 | Peterson et al. | 606/305 |
| 2009/0163962 A1 | 6/2009 | Dauster | |
| 2009/0216280 A1 | 8/2009 | Hutchinson | |
| 2009/0318969 A1* | 12/2009 | Matthis et al. | 606/254 |
| 2010/0152785 A1* | 6/2010 | Forton et al. | 606/301 |
| 2010/0234891 A1 | 9/2010 | Freeman | |
| 2010/0241170 A1 | 9/2010 | Cammisa | |
| 2010/0241171 A1 | 9/2010 | Clement | |
| 2011/0046683 A1 | 2/2011 | Biedermann et al. | |
| 2011/0218579 A1* | 9/2011 | Jackson | 606/305 |
| 2013/0023935 A1* | 1/2013 | Pham et al. | 606/264 |
| 2013/0066380 A1* | 3/2013 | Haskins et al. | 606/305 |
| 2013/0090693 A1* | 4/2013 | Strausbaugh et al. | 606/278 |

* cited by examiner

TWO STEP LOCKING SCREW ASSEMBLY

CROSS REFERENCE TO RELATED APPLICATIONS

This application claims the benefit of priority of U.S. Application Ser. No. 61/524,116, filed Aug. 16, 2011, the contents of which is incorporated by reference herein in its entirety and for all purposes.

FIELD

The present disclosure relates generally to bone fixation assemblies, and more particularly to screw and rod fixation assemblies featuring two step locking mechanisms that provide a compact design and allow the use of smaller and less invasive instrumentation.

BACKGROUND

Surgeons who perform spinal stabilization procedures using pedicle screw systems typically require a mechanism for manipulating the spinal anatomy prior to tightening or locking the pedicle screw system. Manipulation is commonly performed as a distraction or compression of the vertebral disc space. Vertebral body reduction can also be needed, depending on the condition being treated. Manipulation can be carried out with instrumentation that acts on the pedicle screw.

Surgeons often use polyaxial screws to manipulate the spine. Polyaxial screws, which are defined herein as screws that are rotatable about multiple axes of rotation relative to a receiver body, are often chosen because the polyaxicity of the screws provides maneuverability that allows the stabilization construct to be positionally adjusted in multiple directions. The maneuverability of polyaxial screws can be problematic, however, because the freedom of motion can interfere with attempts to apply compression, distraction or reduction. Monoaxial screws, which are defined herein as screws that are rotatable about one and only one axis of rotation relative to a receiver body, are an alternative that avoids the problems associated with polyaxicity. Nevertheless, there is still a large preference for polyaxial screws. Therefore, there is a need for a pedicle screw assembly that allows for the advantages of polyaxial screws while controlling undesired maneuverability of polyaxial screws.

SUMMARY

The drawbacks of conventional screw assemblies are addressed by locking screw assemblies and methods of using locking screw assemblies in accordance with the invention. In one embodiment, a two step locking screw assembly includes a receiving member for receiving a fixation member and an anchor having an enlarged portion and a shank. The enlarged portion of the anchor may be seated in the receiving member. An insert may also extend inside the receiving member. An outer fastener may be positioned in the receiving member. The outer fastener may include a central opening and a pair of ramped flanges. An inner fastener may be disposed inside the central opening of the outer fastener.

In another embodiment, a two step locking screw assembly may include a receiving member for receiving a fixation member. The receiving member may include a tubular body with a first end, a second end, and a tubular wall extending between the first and second ends. The tubular wall may, include an opening in the second end. The tubular wall may also form a passage between the first and second ends. In addition, the tubular wall may form a pair of grooves diametrically opposed to one another inside the tubular body. The assembly may also include an anchor in the form of a polyaxial screw. The screw may include a shank and an enlarged portion in the form of a head. The head may be seated in the passage adjacent the second end. The shank may extend through the opening in the second end. An insert may extend inside the receiving member in the passage. The assembly may include an outer fastener. The outer fastener may have a tubular body that forms a central opening and a pair of ramped flanges diametrically opposed to one another. The ramped flanges may be slidably displaceable into the pair of grooves in the tubular wall. An inner fastener may be disposed inside the central opening of the outer fastener.

In another embodiment, a method can be used to lock a fixation member, such as a fixation rod, inside a screw assembly. The method may include the steps of inserting an insert into a passage in a receiving member. A fixation rod may be inserted through the passage and into a U-shaped channel of the insert. An outer fastener may also be inserted into the passage. An inner fastener may be inserted into the outer fastener. The outer fastener may be rotated until ramped flanges on the outer fastener align with and slide into grooves in the receiving member to drive the outer fastener downwardly against the insert. The outer fastener may be driven downwardly to press the insert against a head of a polyaxial screw to immobilize the screw head in the seat. The inner fastener may be rotated inside the outer fastener to drive the inner fastener downwardly into engagement with the fixation rod. The inner fastener may be driven downwardly against the fixation rod to lock the rod in place in the screw assembly.

BRIEF DESCRIPTION OF THE DRAWINGS

The detailed description that follows will be better understood in conjunction with the drawing figures, of which.

DETAILED DESCRIPTION

Figure 1:
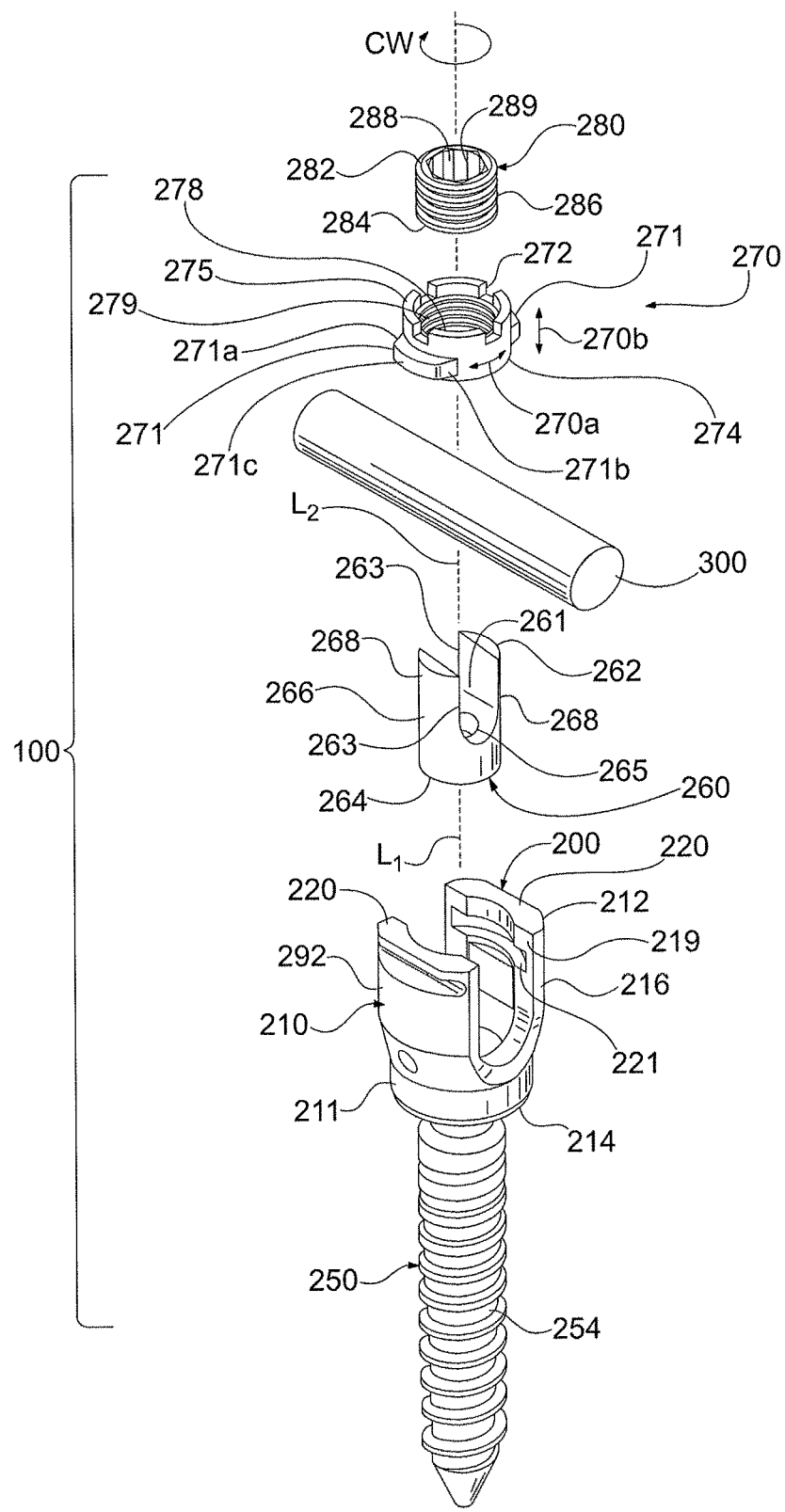
FIG. 1 is an exploded perspective view of a screw and rod fixation assembly in accordance with one exemplary embodiment of the invention.

Although the invention is illustrated and described herein with reference to specific embodiments, the invention is not intended to be limited to the details shown. Rather, various modifications may be made in the details within the scope and range of equivalents of the claims and without departing from the invention.

In one embodiment, a two step locking screw assembly includes a receiving member for receiving a fixation member and a screw having a head and a shank. The head of the screw may be seated in the receiving member. An insert may also extend inside the receiving member. An outer fastener may be positioned in the receiving member. The outer fastener may include a central opening and a pair of ramped flanges. An inner fastener may be disposed inside the central opening of the outer fastener.

The receiving member may include an inner wall into which a pair of grooves are formed. The ramped flanges may be disposed in the grooves in slidable engagement. The outer fastener may include a tubular body having a circumference, with each ramped flange winding around a portion of the circumference and projecting radially outwardly from the tubular body. The tubular body may have a proximal end and a distal end. Each ramped flange extends axially toward the distal end as it winds around the circumference of the tubular body in a clockwise direction.

Each ramped flange may include a first end, a second end and an elongated flange body extending between the first end and the second end. The first end may be located closer to the distal end of the tubular body than the second end, and the second end may be located closer to the proximal end of the tubular body than the first end. The outer fastener may include an internal thread, and the inner fastener may include an external thread mated with the internal thread. The ramp flanges may extend around a portion of the internal thread and the external thread.

In another embodiment, a two step locking screw assembly may include a receiving member for receiving a fixation member. The receiving member may include a tubular body with a first end, a second end, and a tubular wall extending between the first and second ends. The tubular wall may include an opening in the second end. The tubular wall may form a passage between the first and second ends. The tubular wall may form a pair of grooves diametrically opposed to one another inside the tubular body. The assembly may also include a polyaxial screw. The screw may include a head and a shank. The head may be seated in the passage adjacent the second end. The shank may extend through the opening in the second end. An insert may extend inside the receiving member in the passage.

The assembly may further include an outer fastener. The outer fastener may have a tubular body that forms a central opening and a pair of ramped flanges diametrically opposed to one another. The ramped flanges may be slidably displaceable into the pair of grooves in the tubular wall. An inner fastener may be disposed inside the central opening of the outer fastener.

The receiving member may include a midsection between the first and second ends of the receiving member. The first end of the receiving member may include a flange extending radially outwardly from the first end. The flange may include an outer diameter less than the maximum outer diameter of the midsection. The flange and midsection may be separated from one another by a reduced diameter section forming a groove between the flange and midsection. The maximum outer diameter of the reduced diameter section may be less than the maximum outer diameter of the flange.

The ramped flanges may be disposed in the grooves inside the receiving member in slidable engagement. The tubular body of the outer fastener may include a circumference, with each ramped flange winding around a portion of the circumference and projecting radially outwardly from the tubular body of the outer fastener. The outer fastener may include a proximal end and a distal end. Each ramped flange may extend axially toward the distal end of the outer fastener as the ramped flange winds around the circumference of the outer fastener in a clockwise direction.

Each ramped flange may include a first end, a second end and an elongated flange body extending between the first end and the second end of said ramped flange. The first end of each ramped flange is located closer to the distal end of the outer fastener than the second end, and the second end is located closer to the proximal end of the tubular body than the first end. The outer fastener may include an internal thread, and the inner fastener may include an external thread mated with the internal thread. The ramp flanges may extend around a portion of the internal thread and the external thread.

In another embodiment, a method can be used to lock a fixation member, such as a fixation rod, inside a screw assembly. The method may be performed using a screw assembly that includes a receiving member having a tubular body with a first end, a second end, and a tubular wall extending between the first and second ends. The tubular wall may form a passage between the first and second ends.

The tubular wall may form a pair of grooves diametrically opposed to one another inside the tubular body. The screw assembly may also include a polyaxial screw having a head and a shank. The head may be seated in the passage adjacent the second end. The shank may extend through an opening in the second end. The screw assembly may further include an insert having a U-shaped channel. The insert may be configured for placement inside the receiving member in the passage.

The screw assembly may also include an outer fastener having a body that forms a central opening and a pair of ramped flanges diametrically opposed to one another. The ramped flanges may be configured for slidable displacement into the pair of grooves in the tubular wall. The screw assembly may additionally include an inner fastener configured for placement inside the central opening of the outer fastener. The method may include the steps of:

inserting the insert into the passage;

inserting a fixation rod through the passage and into the U-shaped channel of the insert;

inserting the outer fastener into the passage;

inserting the inner fastener into the outer fastener;

rotating the outer fastener until the ramped flanges align with and slide into the grooves in the tubular wall to drive the outer fastener downwardly against the insert;

driving the outer fastener downwardly to press the insert against the head of the polyaxial screw to immobilize the screw head in the seat;

rotating the inner fastener inside the outer fastener to drive the inner fastener downwardly into engagement with the fixation rod; and driving the inner fastener downwardly against the fixation rod to lock the rod in place in the screw assembly.

Figure 2:
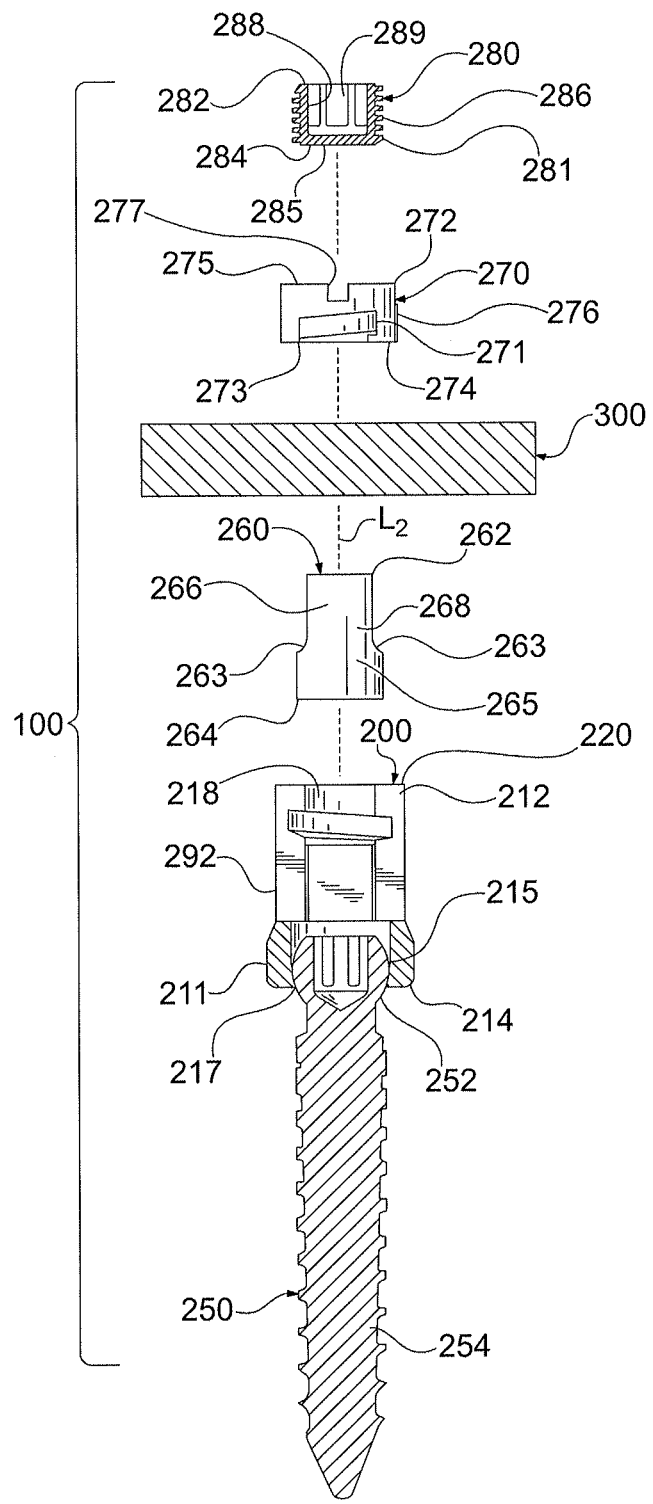
FIG. 2 is an exploded side view of the screw and rod fixation assembly of FIG. 1, with some components viewed in cross section.

Referring to FIGS. 1 and 2, a screw and rod assembly 100 is shown in accordance with one exemplary embodiment of the invention. Assembly 100 includes a two step locking screw assembly 200 and a fixation element in the form of a spinal fixation rod 300. Screw assembly 200 includes a receiving member 210 and a bone anchor in the form of a polyaxial screw 250. Receiving member 210 has a tubular body 211 having a proximal end 212, a distal end 214, a midsection 292, and a tubular wall 216 extending between the proximal and distal ends. Tubular wall 216 has a generally cylindrical shape, defining a longitudinal axis $L_1$. The term "longitudinal axis" as used herein refers to an axis passing through the center point of each cross section of an object, the axis being parallel to the object's longest dimension.

Tubular body 211 has a U-shaped construct, sometimes referred to as a "tulip" or "saddle". The U-shaped construct is defined by a pair of parallel extensions 220 that are generally parallel to longitudinal axis $L_1$. Extensions 220 are separated from one another by an elongated passage 218 that extends from the proximal end 212 to the distal end 214 of receiving member 210. Extensions 220 are also separated from one another by a pair of diametrically opposed slots 219 that extend parallel to the longitudinal axis $L_1$ of tubular body 211. Screw 250 has a frustospherical head 252 configured for polyaxial movement in tubular body 211. In addition, distal end 214 has a hole 217 that extends through the distal end. The diameter of hole 217 is greater than the diameter of the shank 254 but less than the maximum dimension of the screw head 252. In this arrangement, the diameter of shank 254 is small enough to pass through hole 217, while the diameter of head 252 is too large to pass through the hole, so that the head is retained in the receiving member 210. Distal end 214 of receiving member 210 forms a rounded seat 215 inside the receiving member. Head 252 bears against seat 215 and is displaceable in receiving member 210 through a polyaxial range of motion.

Figure 3:
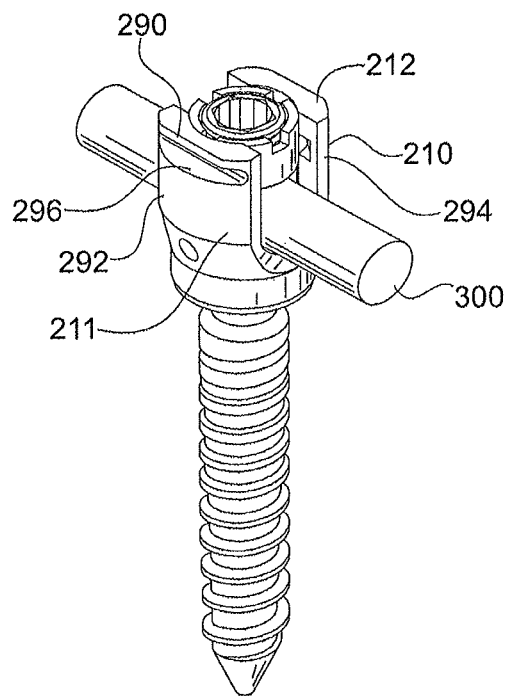
FIG. 3 is a perspective view of the screw and rod fixation assembly of FIG. 1, with components shown in an assembled state.

Screw assembly 200 also includes an insert 260. In the assembled state, insert 260 is positioned beneath rod 300 between the rod and screw head 252. Insert 260 has a U-shaped construct, similar to the receiving member 210. The U-shaped construct is defined by a proximal end 262, a distal end 264 and a tubular body 266 extending between the proximal end and the distal end. Tubular body 266 defines a longitudinal axis $L_2$. Longitudinal axis $L_2$ is preferably coaxial with longitudinal axis $L_1$ when the components are assembled together. A pair of extensions 268 extend generally parallel to longitudinal axis $L_2$. Extensions 268 are separated from one another by an elongated passage 261 and a pair of slots 263. Slots 263 are designed to receive and support rod 300 in a cradled arrangement as shown in FIG. 3. Distal end 264 includes a hole 265 extending through the distal end. The diameter of hole 265 is sized to permit passage of a driver tool to engage the head 252 of bone screw 250.

As noted above, screw assembly 200 is a "two step" locking assembly. A first locking mechanism is deployable to immobilize or "lock down" the polyaxial screw. Once the polyaxial screw is locked down, the orientation of the polyaxial screw is fixed relative to receiving member 210, so that the polyaxial screw can no longer move polyaxially. When first locking mechanisms are deployed in two adjacent screw assemblies 200 to lock down the polyaxial screws, it is easier to apply compression and distraction to the disc space between the adjacent screw assemblies, because the polyaxicity of the screws is restricted and cannot interfere with the compression or distraction. A second locking mechanism is deployable to lock down the fixation rod 300 in receiving member 210.

The first locking mechanism is provided by an outer fastener 270. Outer fastener 270 includes a proximal end 272, a distal end 274 and a tubular body 276 extending between the proximal and distal ends. Tubular body 276 forms a central opening 278 with an inner engagement surface in the form of an internal thread 279. In addition, tubular body 276 includes an outer engagement surface in the form of a pair of ramped flanges 271. Ramped flanges 271 are diametrically opposed to one another on the outer perimeter of tubular body 276, and are configured to mate with a pair of grooves 221 formed in tubular wall 216 of receiving member 210. Grooves 221 are formed in the parallel extensions 220 and are diametrically opposed to one another inside tubular body 211.

Tubular body 276 of outer fastener 270 has a circumference represented by arc shaped arrows 270a in FIG. 1. Each ramped flange 271 winds around a portion of the circumference 270a and projects radially outwardly from tubular body 276 as shown. In addition, each ramped flange 271 extends in an axial direction, represented by arrows 270b. More specifically, each ramped flange 271 extends toward the distal end 274 of outer fastener 270 as the flange winds around the circumference 270a in a clockwise direction CW. Each ramped flange 271 has a first end 271a, a second end 271b and an elongated flange body 271c extending between the first end and the second end. The first end 271a of each ramped flange 271 is located closer to the distal end 274 of tubular body 276 than the second end 271b. The second end 271b of each ramped flange 271 is located closer to the proximal end 272 of tubular body 276 than the first end.

When the components are assembled as shown in FIG. 3, ramped flanges 271 and grooves 221 extend in an axial direction with respect to longitudinal axis $L_1$. Ramped flanges 271 are configured to enter into grooves 221 as outer fastener 270 is rotated inside receiving member 210. Upon rotating outer fastener 270 so that ramped flanges 271 enter into grooves 221, the grooves guide the ramped flanges in an axial direction like a cam to drive the outer fastener downwardly into the receiving member 210. As outer fastener 270 is advanced downwardly, a base portion 273 of the outer fastener bears against proximal end 262 of insert 260. This, in turn, drives insert 260 downwardly so that the distal end 264 of the insert bears against screw head 252. When ramped flanges 271 are completely rotated into grooves 221, outer fastener 270 presses insert 260 downwardly against screw head 252 to compress the screw head against seat 215 and lock down polyaxial screw 250 against polyaxial motion.

Proximal end 272 of outer fastener 270 includes a rim 275 extending around the circumference of the proximal end. Four notches 277 are formed in rim 275, the notches uniformly spaced around the rim at ninety degree intervals as shown. Notches 277 are adapted to couple with a driver tool (not shown).

Figure 6:
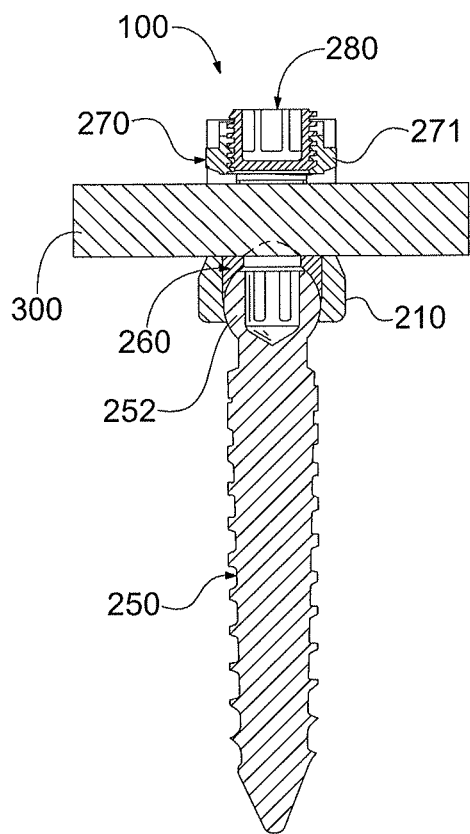
FIG. 6 is a side cross section view of the screw and rod fixation assembly of FIG. 1, taken along line 6-6 of FIG. 4, shown in a first operative state.
Figure 7:
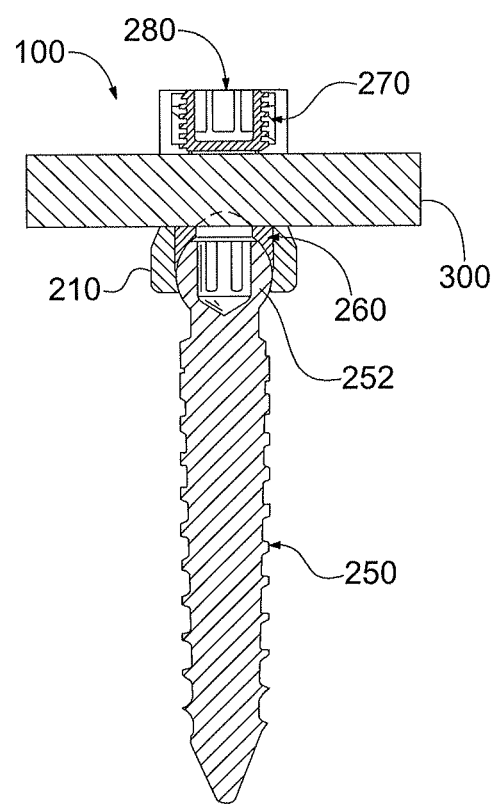
FIG. 7 is a side cross section view of the screw and rod fixation assembly of FIG. 1, taken along line 7-7 of FIG. 5, shown in a second operative state.

The second locking mechanism is provided by an inner fastener 280. Inner fastener 280 includes a proximal end 282, a distal end 284 and a body 286 extending between the proximal and distal ends. Proximal end 282 is open and distal end 284 is closed, the closed distal end forming a distal bearing surface 285. Body 286 surrounds a central opening 288 with an inner engagement surface in the form of a hexagonal socket 289. In addition, tubular body 286 includes an outer engagement surface in the form of an external thread 281. External thread 281 is configured to mate with internal thread 279 in outer fastener 270 to allow inner fastener 280 to be advanced into central opening 278 of the outer fastener. FIGS. 6 and 7 show internal thread 279 and external thread 281 in different mated conditions, as will be described. When internal thread 279 is mated with outer thread 281, the ramp flanges extend around a portion of both the internal thread and the external thread. Consequently, the first locking mechanism is structurally configured with respect to the second locking mechanism to operate around the second locking mechanism, with both locking mechanisms operating inside the receiving member.

When inner fastener 280 is threaded into outer fastener 270, the inner and outer fasteners may be rotatable in unison to begin a two-step locking process. The torque required to rotate inner fastener 280 inside outer fastener 270 is significantly greater than the torque required to rotate the outer fastener in the grooves 221 of receiving member 210. That is, the friction between the threads on the inner fastener 280 and outer fastener 270 provides greater resistance to torque than the surfaces contacting one another between the outer fastener 270 and receiving member 210. Torque applied to the inner fastener 280 nested inside the outer fastener 270 rotates both fasteners in receiving member 210 until ramped flanges 271 contact an end wall in grooves 221. At this point, the outer fastener 270 presses downwardly against insert 260 to lock down the screw 250 relative to the receiving member 210, as described above. The outer fastener 270 also "bottoms out" in the grooves, preventing any further rotation of the outer fastener relative to receiving member 210. Additional torque applied to the inner fastener 280 overcomes the frictional resistance between the threads on the inner fastener and outer fastener 270, and rotates the inner fastener relative to outer fastener 270 to drive the inner fastener downwardly until bearing surface 285 engages rod 300. Once inner fastener 280 is advanced downwardly against rod 300, the rod is locked in place relative to the receiving member 210.

Outer fasteners in accordance with the invention, like outer fastener 270, are preferably designed to avoid the use of a threaded engagement between the outer fastener and the inner wall of the receiving member. This allows the outer fastener to have a non-uniform outer diameter, and in particular, a reduced diameter portion. The absence of threads between the outer fastener and receiving member also allows the receiving member to have a narrow wall thickness around the proximal end of the receiving member where the outer fastener engages the receiving member. These allowances permit the proximal end of the receiving member to have a compact design, which in turn, allows for smaller and less invasive instruments to be attached to the receiving member.

Figure 4:
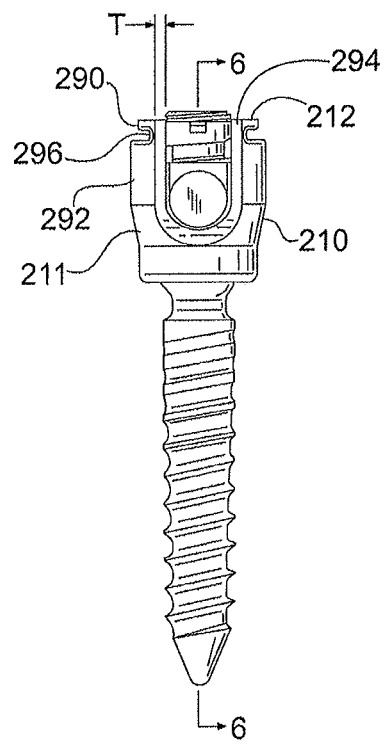
FIG. 4 is a side view of the screw and rod fixation assembly of FIG. 1, shown in a first operative state.
Figure 5:
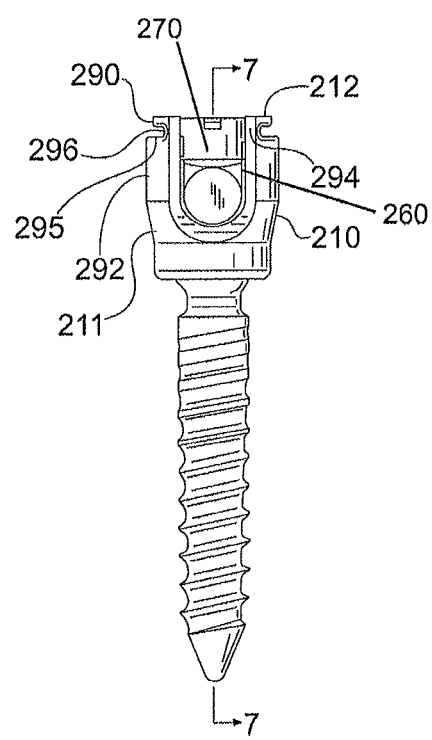
FIG. 5 is a side view of the screw and rod fixation assembly of FIG. 1, shown in a second operative state.

Outer fastener 270 and receiving member 210 embody examples of a compact design in accordance with the invention. Referring to FIG. 1, proximal end 272 of outer fastener 270 has a reduced diameter section as compared to the distal portion that features the ramped flanges 271. Referring to FIGS. 3-5, proximal end 212 includes a flange 290 extending radially outwardly from the proximal end. Flange 290 has an outer diameter less than the maximum outer diameter of the midsection 292 of tubular body 211. The flange 290 and midsection 292 are separated from one another by a reduced diameter section 294. Reduced diameter section 294 features a very thin wall thickness T, which is permitted because the inner wall at the reduced diameter section does not have threads that would require a thicker wall behind them. As such, reduced diameter section 294 forms a groove 296 between the flange and the midsection. The maximum outer diameter of the reduced diameter section 294 is less than the maximum outer diameter of the flange 290, and the maximum outer diameter of the flange is less than the maximum outer diameter of the midsection 292. In this arrangement, the reduced diameter section 294 provides a narrow attachment section 295 for instruments, such as downtubes or extensions, to connect to proximal end 212 of receiving member 210. The narrow attachment section 295 permits tubes that are smaller in cross section than the midsection 292 to connect to the receiving member 210.

Figure 8:
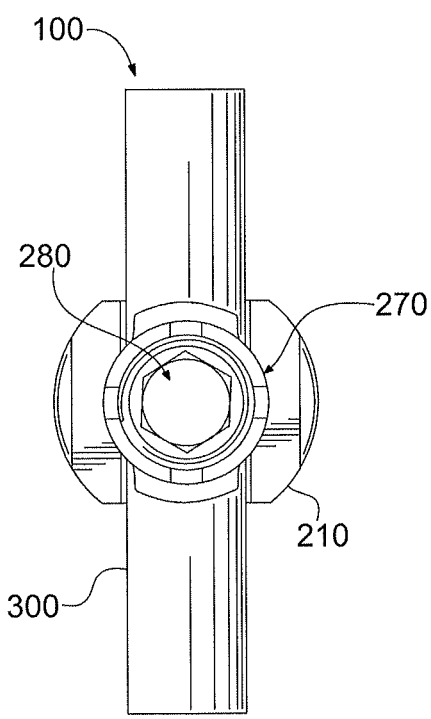
FIG. 8 is a top view of the screw and rod fixation assembly of FIG. 1 in the first operative state shown in FIG. 4.

FIGS. 4, 6 and 8 illustrate screw assembly 220 in a "double unlocked" condition. In this condition, receiving member 210 is "unlocked", meaning it is free to move polyaxially relative to screw head 252. In addition, rod 300 is "unlocked", meaning it is unsecured in receiving member 210. The double unlocked condition allows polyaxial adjustment of receiving member 210 relative to screw 250 after the screw is driven into bone. The double unlocked condition also allows adjustment of the rod's position relative to both the screw 250 and receiving member 210.

Figure 9:
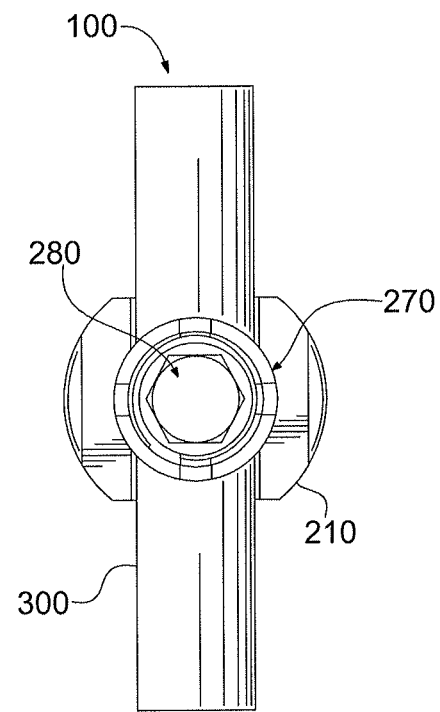
FIG. 9 is a top view of the screw and rod fixation assembly of FIG. 1 in the second operative state shown in FIG. 5.

FIGS. 5, 7 and 9 illustrate screw assembly 220 in a "double locked" condition. In this condition, receiving member 210 is "locked", meaning it is fixed relative to screw head 252 so that it cannot move. In addition, rod 300 is "locked", meaning it is fixed relative to receiving member 210 and screw 250.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the scope of the invention.

What is claimed:

1. A two step locking screw assembly comprising:
a receiving member for receiving a fixation member,
a screw having a head and a shank, the head seated in the receiving member;
an insert extending inside the receiving member, the insert having a proximal end and a distal end;
an outer fastener positioned in the receiving member, the outer fastener having a central opening, a base portion, and a pair of ramped flanges, the base portion of the outer fastener directly engaging the proximal end of the insert, and the distal end of the insert directly engaging the head of the screw, compressing the head of the screw against the receiving member and preventing the screw from moving in polyaxial motion; and
an inner fastener disposed inside the central opening of the outer fastener,
wherein the outer fastener comprises a tubular body, the tubular body comprising a circumference, with each ramped flange winding around a portion of the circumference and projecting radially outwardly from the tubular body, and
wherein the tubular body has a proximal end and a distal end, and wherein each ramped flange extends axially toward the distal end as it winds around the circumference of the tubular body in a clockwise direction.

2. The two step locking screw assembly of claim 1, wherein the receiving member comprises an inner wall into which a pair of grooves are formed.

3. The two step locking screw assembly of claim 2, wherein the ramped flanges are disposed in the grooves in slidable engagement.

4. The two step locking screw assembly of claim 1, wherein each ramped flange has a first end, a second end and an elongated flange body extending between the first end and the second end.

5. The two step locking screw assembly of claim 4, wherein the first end is located closer to the distal end of the tubular body than the second end, and the second end is located closer to the proximal end of the tubular body than the first end.

6. The two step locking screw assembly of claim 1, wherein the outer fastener comprises an internal thread, and the inner fastener comprises an external thread mated with the internal thread.

7. The two step locking screw assembly of claim 6, wherein the ramp flanges extend around a portion of the internal thread and the external thread.

8. A two step locking screw assembly comprising:
a receiving member comprising a tubular body with a first end, a second end, and a tubular wall extending between the first and second ends, the tubular wall having an opening in the second end, the tubular wall forming a passage between the first and second ends, the tubular wall forming a pair of grooves diametrically opposed to one another inside the tubular body;
a polyaxial screw having a head and a shank, the head seated in the passage adjacent the second end, and the shank extending through the opening in the second end;
an insert extending inside the receiving member in the passage, the insert having a proximal end and a distal end;
an outer fastener having a tubular body that forms a central opening, a base portion, and a pair of ramped flanges diametrically opposed to one another, the ramped flanges slidably displaceable into the pair of grooves in the tubular wall, the base portion of the outer fastener directly engaging the proximal end of the insert, and the distal end of the insert directly engaging the head of the polyaxial screw, compressing the head of the polyaxial screw against the receiving member and preventing the polyaxial screw from moving in polyaxial motion;
an elongated fixation member received within the receiving member and disposed between the outer fastener and the insert; and
an inner fastener disposed inside the central opening of the outer fastener,
wherein the tubular body of the outer fastener comprises a circumference, with each ramped flange winding around a portion of the circumference and projecting radially outwardly from the tubular body of the outer fastener, and
wherein the outer fastener has a proximal end and a distal end, and wherein each ramped flange extends axially toward the distal end of the outer fastener as said ramped flange winds around the circumference of the outer fastener in a clockwise direction.

9. The two step locking screw assembly of claim 8, wherein the receiving member comprises a midsection between the first and second ends of the receiving member, the first end of the receiving member comprising a flange extending radially outwardly from the first end, the flange having an outer diameter less than the maximum outer diameter of the midsection, the flange and midsection separated from one another by a reduced diameter section forming a groove between the flange and midsection, the maximum outer diameter of the reduced diameter section being less than the maximum outer diameter of the flange, and the maximum outer diameter of the flange being less than the maximum outer diameter of the midsection.

10. The two step locking screw assembly of claim 8, wherein the ramped flanges are disposed in the grooves inside the receiving member in slidable engagement.

11. The two step locking screw assembly of claim 8, wherein each ramped flange has a first end, a second end and an elongated flange body extending between the first end and the second end of said ramped flange.

12. The two step locking screw assembly of claim 11, wherein the first end of each ramped flange is located closer to the distal end of the outer fastener than the second end of said ramped flange, and the second end is located closer to the proximal end of the tubular body than the first end.

13. The two step locking screw assembly of claim 8, wherein the outer fastener comprises an internal thread, and the inner fastener comprises an external thread mated with the internal thread.

14. The two step locking screw assembly of claim 13, wherein the ramp flanges extend around a portion of the internal thread and the external thread.

15. A method of locking a fixation rod inside a screw assembly, the screw assembly comprising a receiving member having a tubular body with a first end, a second end, and a tubular wall extending between the first and second ends, the tubular wall forming a passage between the first and second ends, the tubular wall forming a pair of grooves diametrically opposed to one another inside the tubular body, a polyaxial screw having a head and a shank, the head seated in the passage adjacent the second end, and the shank extending through an opening in the second end, an insert having a proximal end, a distal end and a U-shaped channel wherein the insert is configured for placement inside the receiving member in the passage, an outer fastener having a body that includes a base portion and forms a central opening and a pair of ramped flanges diametrically opposed to one another, the ramped flanges configured for slidable displacement into the pair of grooves in the tubular wall, and an inner fastener configured for placement inside the central opening of the outer fastener, the method comprising the steps of:
inserting the insert into the passage;
inserting a fixation rod through the passage and into the U-shaped channel of the insert;
inserting the outer fastener into the passage;
inserting the inner fastener into the outer fastener;
rotating the outer fastener until the ramped flanges align with and slide into the grooves in the tubular wall to drive the outer fastener downwardly against the insert;
driving the outer fastener downwardly wherein the base portion of the outer fastener directly engages the proximal end of the insert, and the distal end of the insert presses against the head of the polyaxial screw to immobilize the screw head in the seat;
rotating the inner fastener inside the outer fastener to drive the inner fastener downwardly into engagement with the fixation rod; and
driving the inner fastener downwardly against the fixation rod to lock the rod in place in the screw assembly.

* * * * *